(12) United States Patent
Akahori

(10) Patent No.: US 12,429,449 B2
(45) Date of Patent: Sep. 30, 2025

(54) BIOMOLECULE ANALYSIS METHOD, BIOMOLECULE ANALYZING REAGENT, AND BIOMOLECULE ANALYSIS DEVICE

(71) Applicant: HITACHI HIGH-TECH CORPORATION, Tokyo (JP)

(72) Inventor: Rena Akahori, Tokyo (JP)

(73) Assignee: HITACHI HIGH-TECH CORPORATION, Tokyo (JP)

( * ) Notice: Subject to any disclaimer, the term of this patent is extended or adjusted under 35 U.S.C. 154(b) by 345 days.

(21) Appl. No.: 18/018,084

(22) PCT Filed: Jul. 31, 2020

(86) PCT No.: PCT/JP2020/029403
§ 371 (c)(1),
(2) Date: Jan. 26, 2023

(87) PCT Pub. No.: WO2022/024335
PCT Pub. Date: Feb. 3, 2022

(65) Prior Publication Data
US 2023/0266264 A1    Aug. 24, 2023

(51) Int. Cl.
*G01N 27/327* (2006.01)
*C12Q 1/6869* (2018.01)
*G01N 27/414* (2006.01)

(52) U.S. Cl.
CPC ....... *G01N 27/3278* (2013.01); *C12Q 1/6869* (2013.01); *G01N 27/4145* (2013.01); *G01N 27/4146* (2013.01)

(58) Field of Classification Search
None
See application file for complete search history.

(56) References Cited

U.S. PATENT DOCUMENTS

| | | | |
|---|---|---|---|
| 5,795,782 A | 8/1998 | Church et al. | |
| 2016/0023239 A1 | 1/2016 | Golovchenko et al. | |
| 2018/0074006 A1* | 3/2018 | Goto ............... | G01N 33/48721 |

(Continued)

FOREIGN PATENT DOCUMENTS

| | | |
|---|---|---|
| JP | 2016-522735 A | 8/2016 |
| JP | 2020-085578 A | 6/2020 |
| WO | 2018131064 A1 | 7/2018 |

(Continued)

OTHER PUBLICATIONS

Office Action mailed Jan. 30, 2024 in Japanese Application No. 2022-539932.

(Continued)

*Primary Examiner* — J. Christopher Ball
(74) *Attorney, Agent, or Firm* — Miles & Stockbridge, P.C.

(57) ABSTRACT

A biomolecule analysis method of the present disclosure includes: preparing a biomolecule analysis device including a thin film, a first liquid tank and a second liquid tank separated by the thin film, a first electrode disposed in the first liquid tank, and a second electrode disposed in the second liquid tank; and forming a nanopore in the thin film by applying a first voltage between the first electrode and the second electrode in a state where a nanopore forming solution is enclosed in the first liquid tank and the second liquid tank, wherein the nanopore forming solution contains ammonium ions and sulfate ions.

24 Claims, 12 Drawing Sheets

(56) References Cited

U.S. PATENT DOCUMENTS

2019/0353636 A1 11/2019 Matsui et al.
2021/0293750 A1 9/2021 Akahori et al.

FOREIGN PATENT DOCUMENTS

WO 2020044780 A1 3/2020
WO 2020084705 A1 4/2020

OTHER PUBLICATIONS

Search Report mailed Oct. 20, 2020 in International Application No. PCT/JP2020/029403.
Written Opinion mailed Oct. 20, 2020 in International Application No. PCT/JP2020/029403.
Cherf, et al., "Automated forward and reverse ratcheting of DNA in a nanopore at 5-A precision" Nature Biotechnology, vol. 30, No. 4, Apr. 2012, pp. 344-348.
Yanagi et al., "Fabricating nanopores with diameters of sub-1 nm to 3 nm using multilevel pulse-voltage injection" Scientific Reports, 4, 5000, May 2014, pp. 1-7.
Akahori et al., "Slowing single-stranded DNA translocation through a solid-state nanopore by decreasing the nanopore diameter" Nanotechnology, 25, Mar. 2014, pp. 1-6.
Laszlo et al., "Decoding long nanopore sequencing reads of natural DNA" Nature Biotechnology, 32(8), Aug. 2014, pp. 1-13.
Yanagi et al., "Fabrication of 3-nm-thick Si3N4 membranes for solid-state nanopores using the poly-Si sacrificial layer process" Scientific Reports, 5,14656, Mar. 2015, pp. 1-13.
Goto et al., "Deceleration of single-stranded DNA passing through a nanopore using a nanometre-sized bead structure" Scientific Reports, 5, 16640, pp. 1-8, 2015.
Storm et al., "Fabrication of solid-state nanopores with single-nanometre precision" Nature Materials, vol. 2, Aug. 2003, pp. 537-541.
Office Action mailed Jul. 8, 2025 in Japanese Application No. 2022-539932.

* cited by examiner

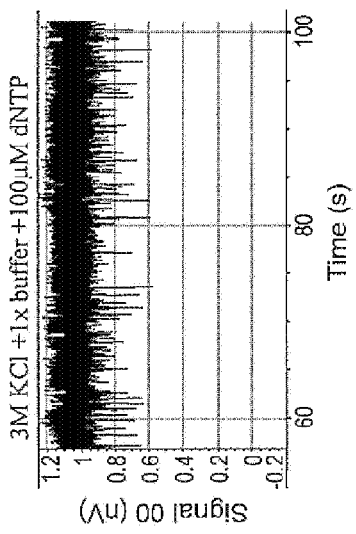
FIG. 6A
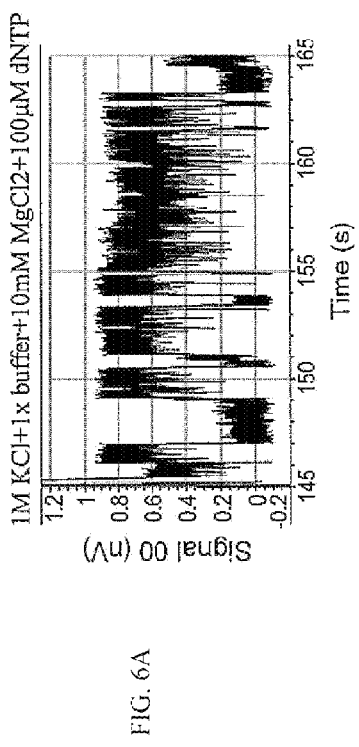
FIG. 6B
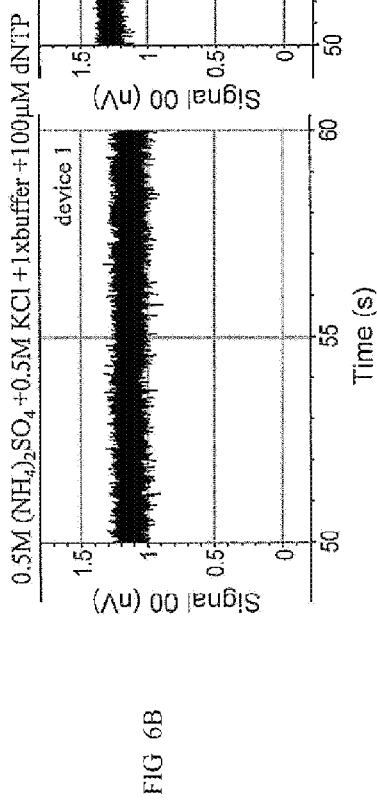
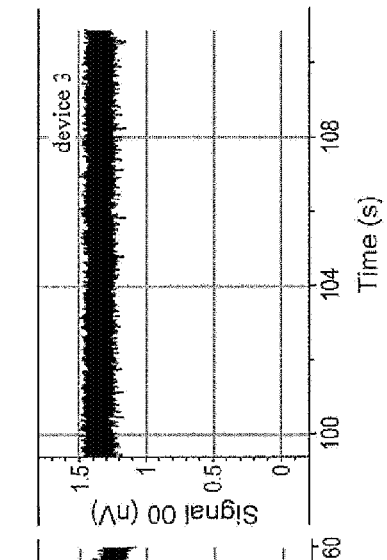
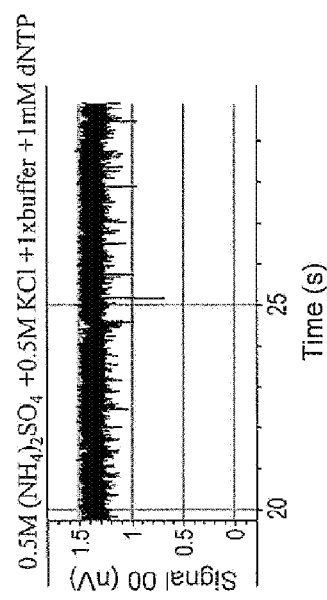
FIG. 6C

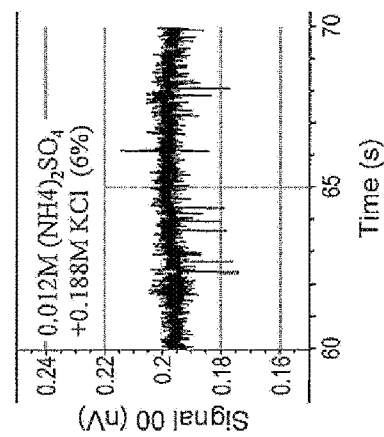
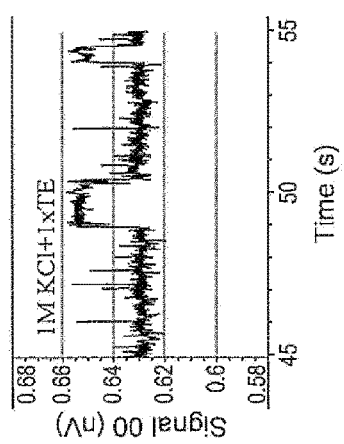
FIG. 8A
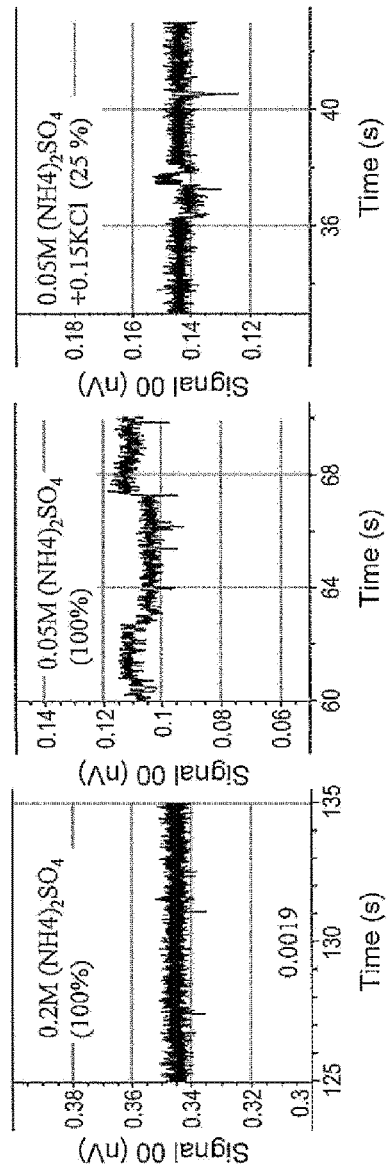
FIG. 8B

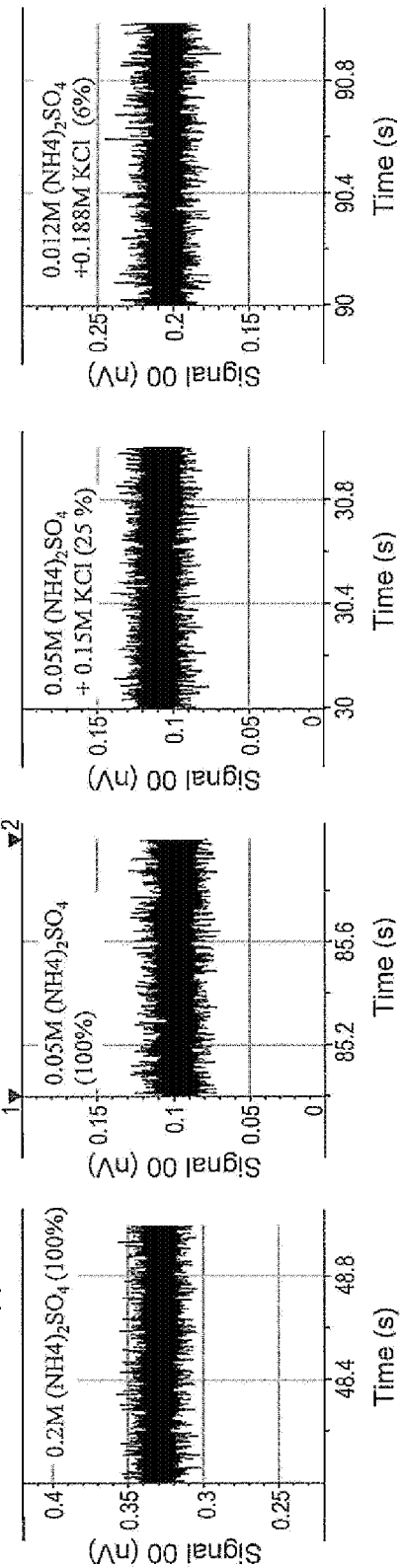
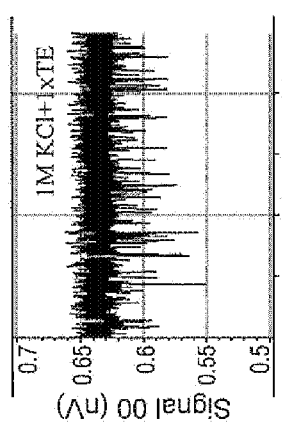
FIG. 9A
FIG. 9B

BIOMOLECULE ANALYSIS METHOD, BIOMOLECULE ANALYZING REAGENT, AND BIOMOLECULE ANALYSIS DEVICE

TECHNICAL FIELD

The present disclosure relates to a biomolecule analysis method, a biomolecule analyzing reagent, and a biomolecule analysis device.

BACKGROUND ART

In the field of next-generation DNA sequencers, a method for electrically and directly measuring the base sequence of DNA without performing an extension reaction or a fluorescent label has attracted attention. Specifically, research and development of nanopore DNA sequencing methods have been actively promoted. This method is a method for directly measuring a DNA strand without using a reagent to determine a base sequence.

In the nanopore DNA sequencing method, the base sequence is measured by measuring a blockade current generated by a DNA strand passing through a pore (hereinafter, referred to as "nanopore") formed in a thin film. Since the blockade current changes depending on the difference between individual base species contained in the DNA strand, the base species can be sequentially identified by measuring the amount of the blockade current. In this method, since information of the DNA strand is directly obtained, DNA of a long strand can be decoded in principle, and modification to the DNA strand can also be directly decoded.

A biomolecule analysis device is used when analyzing DNA in the nanopore DNA sequencing method. The biomolecule analysis device generally includes first and second liquid tanks filled with an electrolyte solution, a thin film for partitioning the first and second liquid tanks, and first and second electrodes respectively provided in the first and second liquid tanks. The biomolecule analysis device can also be configured as an array device. The array device refers to a device including a plurality of sets of liquid chambers partitioned by a thin film. For example, the first liquid tank is used as a common tank. The second liquid tank is used for a plurality of individual tanks. In this case, electrodes are disposed in the common tank and each of the individual tanks.

In this configuration, when a voltage is applied between the first liquid tank and the second liquid tank, an ionic current (baseline current) corresponding to the diameter of the nanopore flows through the nanopore. A potential gradient is formed in the nanopore in accordance with the applied voltage. When a biomolecule such as DNA is introduced into the first liquid tank, the biomolecule is transported to the second liquid tank via the nanopore in response to the diffusion and the potential gradient. At this time, biomolecular analysis is performed in accordance with the blockade rate of each nucleic acid that blocks the nanopore. The biomolecule analysis device includes a measurement unit that measures an ionic current (blockade signal) flowing between the first and second electrodes provided in the biomolecule analysis device. The measurement unit obtains sequence information of biomolecules based on the value of the measured ion current (blockade signal).

Here, when noise is included in the baseline current, the noise is superimposed on the blockade signal. Thus, research and development have been promoted for reducing the noise included at the stage of measuring the baseline current.

One of noise sources is RIN noise. This noise is considered to be generated by bonding or separating electrons or ions constituting an electrolyte to or from a dangling bond present on the surface of a semiconductor material such as SiN.

PTL 1 describes, as a technique for reducing RTN noise, "a current measurement device including: a first tank; a second tank; a thin film, disposed between the first tank and the second tank, having a nanopore that communicates the first tank and the second tank; a first electrode provided in the first tank; and a second electrode provided in the second tank, wherein: a wall surface of the nanopore has an ion adsorption prevention structure that prevents the desorption and adsorption of ions contained in a solution filled in the first tank and/or the second tank; and an ion current passing through the nanopore is measured by applying a voltage between the first electrode and the second electrode" (see claim 1 of PTL 1).

In order to decode the biomolecule in detail, it is necessary to transport the biomolecule at a speed equal to or lower than the response speed of an amplifier. As one of methods for controlling the transport speed of the biomolecule, a method using an enzyme represented by polymerase or helicase as a molecular motor has been proposed (NPL 1).

CITATION LIST

Patent Literature

PTL 1: WO 2018/131064

Non-Patent Literature

NPL 1: Cherf, G., Lieberman, K., Rashid, H. et al., Nature Biotechnology 30, 344-348 (2012)

SUMMARY OF INVENTION

Technical Problem

As in NPL 1, in order to maintain the activity of the enzyme as the molecular motor, a substrate having a high concentration is required. However, the substrate present in a solution also becomes the noise source of the baseline current. Since the substrate also has a negative charge, the substrate passes through the nanopore to become a signal source.

In PTL 1, the suppression of noise caused by the substrate in the solution has not been studied at all.

Therefore, the present disclosure provides a technique for suppressing noise derived from a substrate while suppressing the noise of a baseline current.

Solution to Problem

A biomolecule analysis method according to an aspect of the present disclosure includes: preparing a biomolecule analysis device including a thin film, a first liquid tank and a second liquid tank separated by the thin film, a first electrode disposed in the first liquid tank, and a second electrode disposed in the second liquid tank; and forming a nanopore in the thin film by applying a first voltage between the first electrode and the second electrode in a state where a nanopore forming solution is enclosed in the first liquid tank and the second liquid tank, wherein the nanopore forming solution contains ammonium ions and sulfate ions.

A biomolecule analysis method according to another aspect of the present disclosure includes: preparing a biomolecule analysis device including a thin film having a nanopore, a first liquid tank and a second liquid tank separated by the thin film, a first electrode disposed in the first liquid tank, and a second electrode disposed in the second liquid tank; and measuring a current flowing between the first electrode and the second electrode by applying a voltage between the first electrode and the second electrode in a state where a measurement solution is enclosed in the first liquid tank and the second liquid tank, wherein the measurement solution contains ammonium ions and sulfate ions.

Other features related to the present disclosure will be clear from the description and the accompanying drawings of the present specification. In addition, the aspects of the present disclosure are achieved and realized by elements, combinations of various elements, the following detailed description, and aspects of the appended claims.

The description of the present specification is given only as a typical example, and does not limit the scope of claims or application examples of the present disclosure in any manner.

Advantageous Effects of Invention

According to the technology of the present disclosure, it is possible to reduce the noise of a baseline current after a nanopore is formed can be reduced and to suppress noise derived from a substrate.

The problems, constitutions, and effects other than those described above are apparent from the descriptions of the following embodiments.

BRIEF DESCRIPTION OF DRAWINGS

FIGS. 6A-6C are graphs showing the result of Experimental Example 3.

FIGS. 8A and 8B are graphs showing the result of Experimental Example 5.

FIGS. 9A and 9B are graphs showing the result of Experimental Example 6.

DESCRIPTION OF EMBODIMENTS

Hereinafter, embodiments of the present disclosure will be described with reference to the drawings. Although the accompanying drawings illustrate specific embodiments based on the principles of the present disclosure, the drawings are provided for understanding the technology of the present disclosure, and are not used for restrictively interpreting the present disclosure.

In the present disclosure, a "biopolymer (biomolecule)" refers to, for example, a nucleic acid (DNA, RNA, PNA, or oligonucleotide or the like), a protein, or a nucleic acid in which a protein is modified, and may be a natural product or an artificial product.

In the present disclosure, the "analysis" of the biopolymer refers to the characteristic analysis of the biopolymer. Examples of the characteristic analysis of the biopolymer include analysis (sequence determination) of the sequence order of a nucleic acid monomer, determination of a nucleic acid length, detection of a single base polymorphism, determination of the number of biopolymers, and detection of a conformation polymorphism in a biopolymer (a copy number polymorphism, insertion, or deletion or the like).

[Biomolecule Analysis Method]

Figure 1:
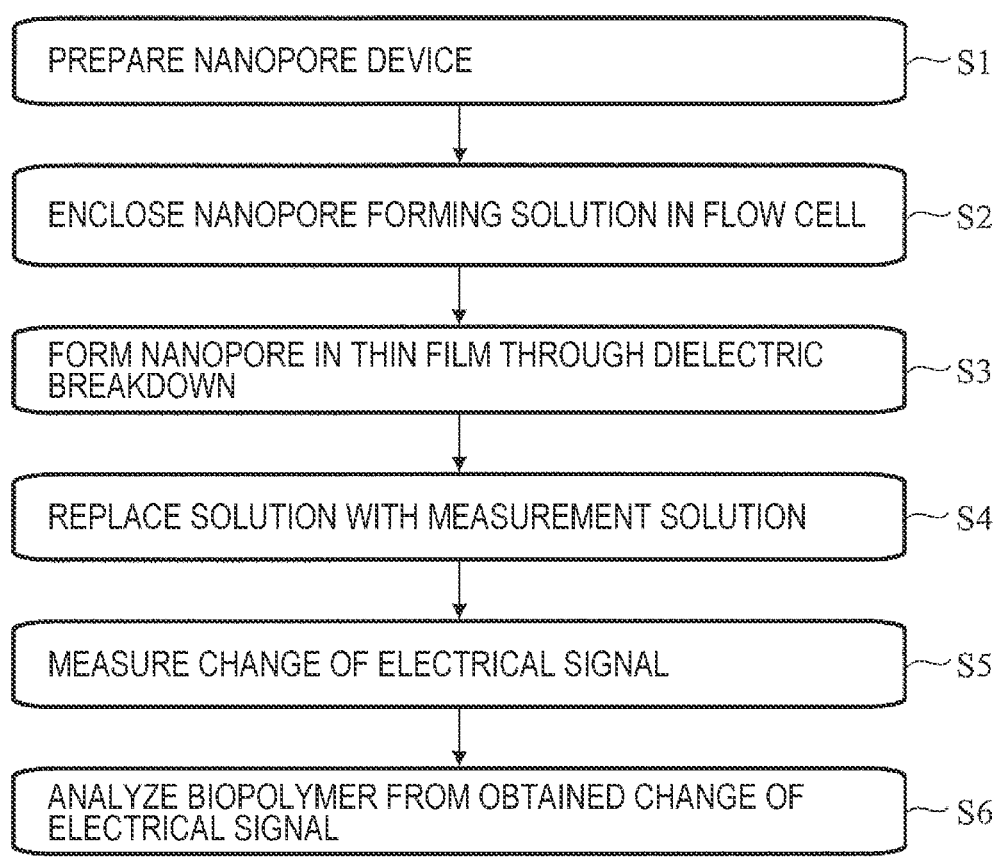
FIG. 1 is a flowchart showing a biomolecule analysis method.

FIG. 1 is a flowchart showing a biomolecule analysis method according to a first embodiment.

(Step S1: Preparation of Nanopore Device)

In step S1, an operator prepares a nanopore device (biomolecule analysis device). In the present embodiment, it is decided that a solid-state nanopore device is prepared. Specifically, for example, the nanopore device includes a thin film in which a nanopore is to be formed, and can be formed by installing a thin film in a flow cell. As a result, liquid tanks are formed on both sides of the thin film. A first electrode is disposed in one liquid tank (first liquid tank). A second electrode is disposed in the other liquid tank (second liquid tank). A power source is connected to the first electrode and the second electrode to apply a voltage between the first electrode and the second electrode. The operator installs an ammeter that measures a current between the first electrode and the second electrode.

(Step S2: Enclosure of Nanopore Forming Solution)

In step S2, the operator encloses a nanopore forming solution (electrolyte solution) for opening a nanopore in the first liquid tank and the second liquid tank from a supply port of the flow cell.

(Step S3: Opening of Nanopore)

In step S3, the operator drives a power source to apply a voltage for opening a nanopore between the first electrode and the second electrode, thereby forming the nanopore in the thin film by dielectric breakdown.

(Step S4: Replacement to Measurement Solution)

In step S4, the operator discharges the nanopore forming solution from a discharge port of the flow cell to enclose a measurement solution (electrolyte solution) containing a biopolymer to be analyzed and having affinity for a biopolymer from the supply port of the flow cell. As a result, the electrolyte solution in the first liquid tank and the second liquid tank is replaced.

(Step S5: Measurement)

In step S5, the operator drives the power source to apply a voltage for analysis between the first electrode and the second electrode so that the voltage transports a nucleic acid to pass through the nanopore. At this time, the operator uses an ammeter to measure a change of an electrical signal (current value) from the first electrode and the second electrode.

(Step S6: Analysis of Biopolymer)

In step S6, for example, the operator uses a computer device to analyze the biopolymer based on the change of the electrical signal. When the biopolymer passes through the nanopore, the electrical signal changes according to the types of the bases, so that the sequence can be determined according to the pattern of the electrical signal. Such a method is disclosed in detail in the literature (A. H. Laszlo et al., Nat Biotechnol. 32, 829, 2014). As another application, the number of the biopolymers contained in the solution can also be determined by the total number of the biopolymers passing through the nanopore.

(Regarding Electrolyte Solution)

As a result of intensive studies on the electrolyte solution, the present inventor has unexpectedly found that noise in a baseline current can be prevented when a nanopore forming solution or a measurement solution containing ammonium ions as cations of an electrolyte and sulfate ions as anions is used and that noise derived from a substrate contained in the solution can also be prevented when a molecular motor is used.

Therefore, in the biomolecule analysis method of the present embodiment, at least one of the nanopore forming solution and the measurement solution (hereinafter, may be simply referred to as "electrolyte solution") contains the ammonium ions ($NH_4^+$) as the cations of the electrolyte and also contains the sulfate ions ($SO_4^{2-}$) as the anions. That is, the electrolyte of the electrolyte solution generates the ammonium ions as the cations and the sulfate ions as the anions. Both the nanopore forming solution and the measurement solution can also contain the ammonium ions and the sulfate ions.

Ammonium sulfate, for example, can be used as the electrolyte (salt) that generates the ammonium ions and the sulfate ions. A sulfate salt and an ammonium salt that ionize in a solvent can also be used ss the electrolyte. Examples of the sulfate salt include a sulfate salt in which ions generated upon ionization are monovalent cations (for example, lithium sulfate, cesium sulfate, sodium sulfate, and potassium sulfate and the like) and a sulfate salt in which ions generated upon ionization are divalent cations (for example, magnesium sulfate, calcium sulfate, copper sulfate, and iron sulfate and the like). Examples of the ammonium salt include ammonium chloride and ammonium carbonate.

In order to ensure electrical conductivity, the electrolyte solution may contain ions other than the ammonium ions and the sulfate ions. The cations can be selected from, for example, any metal ions. However, for example, monovalent metal ions such as potassium ions may promote the bond dissociation of dangling bonds on an SiN surface. Divalent metal ions have a certain effect on reduction in noise superimposed on the baseline current. But, when the divalent metal ions are present at a high concentration, the divalent metal ions cause a decrease in the activity of the molecular motor used to transport the biopolymer. Therefore, when cations other than the ammonium ions are contained in the electrolyte solution, it is necessary to suitably adjust the type and concentration thereof. The anions can be selected depending on the compatibility with the material of the electrode. For example, when silver halide is used as the material of the electrode, the anions contained in the electrolyte solution may be halide ions (chloride ions, bromide ions, or iodide ions). Alternatively, the anions may be organic anions typified by glutamic acid ions and the like.

That is, it is possible to allow the ammonium sulfate or an electrolyte (salt) other than the sulfate salt and the ammonium salt to coexist in the electrolyte solution. Examples of such an electrolyte include KCl, NaCl, LiCl, and CsCl. When platinum or Au is used for the electrode, ferricyanide or ferrocyanide may be allowed to coexist. When the molecular motor is used as one means for performing any transport control of the biopolymer, a substrate and a buffer suitable for driving the molecular motor are allowed to coexist in the electrolyte solution in the first liquid tank. In order to stabilize the biopolymer, a buffering agent can also be mixed. In general, $MgSO_4$, $MgCl_2$, Tween (registered trademark), HEPES, Tris-HCl, EDTA, or glycerol or the like can be mixed as the buffering agent.

As a solvent for the electrolyte solution, it is possible to use a solvent which can stably disperse the biopolymer but neither dissolve an electrode nor inhibit electron transfer with the electrode. Examples of the solvent of the electrolyte solution include water, alcohols (methanol, ethanol, and isopropanol and the like), acetic acid, acetone, acetonitrile, dimethylformamide, and dimethylsulfoxide. When a nucleic acid as the biopolymer is used as an object to be measured, water is typically used.

By providing the lower limit of the concentration of the electrolyte, a signal-to-noise ratio can be improved. Specifically, for example, the lower limit of the concentration of the electrolyte can be set to 0.01 M. Meanwhile, there is no requirement to inhibit the upper limit of the concentration of the electrolyte, which allows the saturation concentration to be tolerated. That is, when the electrolyte solution contains only the ammonium sulfate as the electrolyte (salt), the concentration of the ammonium sulfate can be set to 0.01 M or more and a saturation concentration or less. The concentration the ammonium sulfate can be optionally set to 0.01 M or more and 1 M or less, or 0.01 M or more and 0.2 M or less, in accordance with some situation.

When the electrolyte solution contains the ammonium sulfate and the other salts as the electrolyte (salt), it is possible to set to 5% or more and less than 100% the ratio of the concentration of the ammonium sulfate to the total concentration of the salts. It is possible to optionally set to 25% or more and less than 100%, or 50% or more and less than 100% the ratio of the concentration of the ammonium sulfate to the total concentration of the salts, in accordance with some situation.

When the electrolyte solution contains the sulfate salt, the ammonium salt and the other salts as the electrolyte, it is possible to set to 5% or more and less than 100% the ratio of the concentration of the sulfate ions to the total concentration of the anions. It is possible to optionally set to 25% or more and less than 100%, or 50% or more and less than 100% the ratio of the concentration of the sulfate ions to the total concentration of the anions, in accordance with some situation. It is possible to set to 5% or more and less than 100% the ratio of the concentration of the ammonium ions to the total concentration of the cations. It is possible to optionally set to 258 or more and less than 100%, or 50% or more and less than 100% the ratio of the concentration of the ammonium ions to the total concentration of the cations, in accordance with some situation.

As explained above, at least one of the nanopore forming solution and the measurement solution is the electrolyte solution containing the ammonium ions and the sulfate ions. Meanwhile, the nanopore can be formed not only by dielectric breakdown but also by preliminary microfabrication or processing using a TEM device. In this case, in above-described step S1, the operator assembles the nanopore device using the thin film in which the nanopore is preliminarily formed, and does not perform steps S2 and S3.

The measurement can also be performed using the nanopore forming solution without replacing the nanopore forming solution used in steps S2 and S3 with the measurement solution. Meanwhile, the biopolymer can be more accurately analyzed by replacing the nanopore forming solution with the measurement solution that is more suitable for the biopolymer as in the above-described step S4.

Furthermore, although the case of using the solid state nanopore device as the biomolecule analysis device has been described, the same operation can be applied to a biological nanopore device. In the case of using the biological nanopore device, the above-described steps S2 and S3 are not performed but a measurement solution containing ammonium ions and sulfate ions is introduced in step S4.

(Conclusion)

As described above, in the biomolecule analysis method according to the present embodiment, at least one of the nanopore forming solution and the measurement solution contains the ammonium ions as the cations and the sulfate ions as the anions. Otherwise, the biomolecular analysis method can be performed using the same apparatus, steps, and conditions as those in the conventional method. The use of such a nanopore forming solution or measurement solution allows to prevent RIN with respect to the baseline current and the noise derived from the substrate contained in the measurement solution and to smoothly and correctly measure the blockade current in the nanopore.

[Biomolecule Analyzing Reagent]

The biomolecule analyzing reagent of the present disclosure contains the electrolyte of the above-described electrolyte solution as a constituent element. That is, the biomolecule analyzing reagent contains ammonium ions as cations and sulfate ions as anions when being formed into a solution. The biomolecule analyzing reagent is used as at least one of the nanopore forming reagent and the measurement reagent.

The biomolecule analyzing reagent of the present disclosure may be provided together with the instructions describing the use procedure and use amount thereof and the like. The biomolecule analyzing reagent may be provided in a ready-to-use state (the above-described nanopore forming solution and measurement solution), as a concentrated solution for dilution with an appropriate solvent during use, or in a solid state for reconstitution with a suitable solvent during use (for example, powder and the like). Those skilled in the art could understand the embodiment and preparation of such a biomolecule analyzing reagent.

The nanopore forming reagent is used when the voltage is applied between the two liquid tanks formed on both sides of the thin film to form the nanopore by dielectric breakdown. The measurement reagent is used in passing the biopolymer through the nanopore and measuring the current (blockade current) flowing through the nanopore. The concentration of the electrolyte of the nanopore forming reagent and the concentration of the electrolyte of the measurement reagent may be the same or different from each other. Only one of the nanopore forming reagent and the measurement reagent may contain the electrolyte of the above-described electrolyte solution as the constituent element, and the other may be a reagent having a conventional composition. These reagents may be provided to a user as a set of the nanopore forming reagent and the measurement reagent, or may be separately provided.

(Conclusion)

As described above, the biomolecule analyzing reagent according to the present embodiment generates the ammonium ions as the cations and the sulfate ions as the anions when at least one of the nanopore forming solution and the measurement solution is used. The use of such a biomolecule analysis reagent allows to prevent the RTN with respect to the baseline current and the noise derived from the substrate contained in the measurement solution and to smoothly and correctly measure the blockade current in the nanopore.

[Biomolecule Analysis Device]

Figure 2:
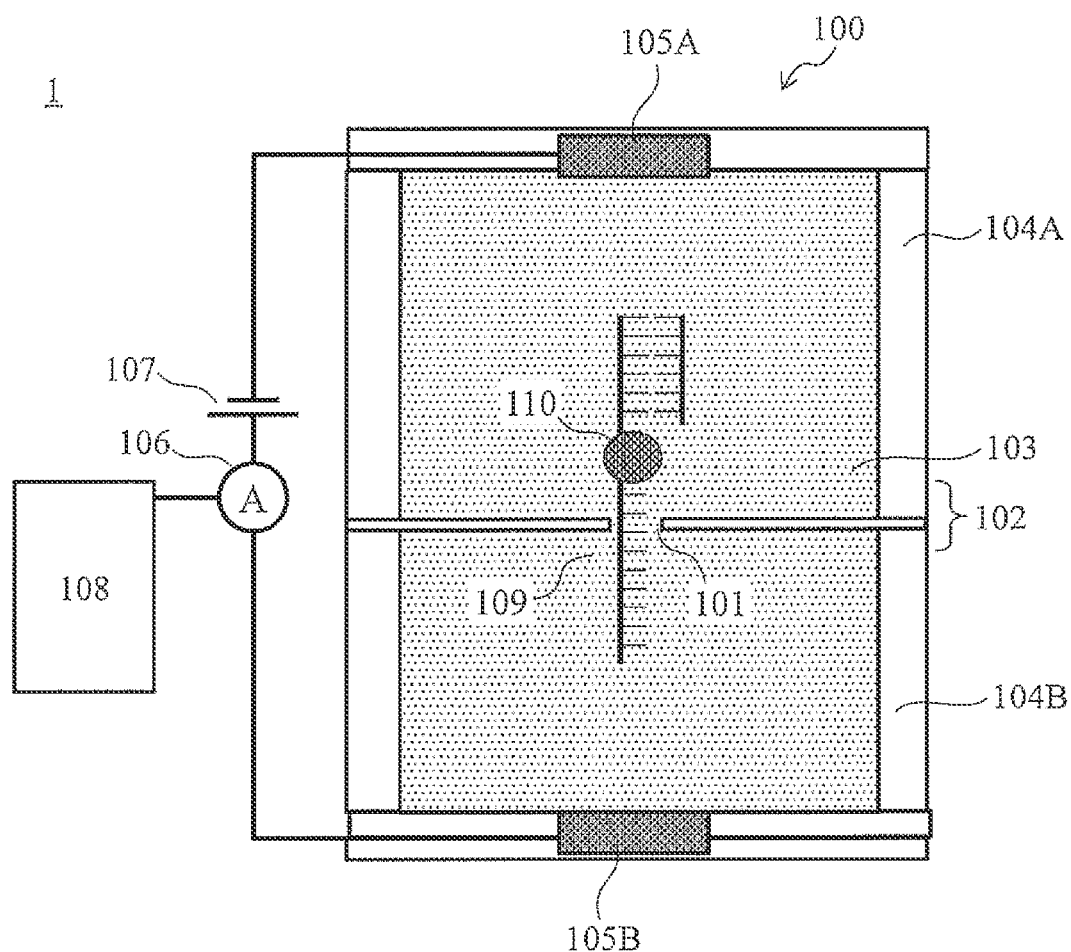
FIG. 2 is a schematic cross-sectional view showing the configuration of a biomolecule analysis device.

FIG. 2 is a schematic cross-sectional view showing the configuration of a biomolecule analysis device 1 according to the first embodiment. The biomolecule analysis device 1 is a device that measures an ion current according to a blockade current method. As shown in FIG. 2, the biomolecule analysis device 1 includes a nanopore device 100, an ammeter 106, a power source 107, and a computer 108. The nanopore device 100 includes a thin film 102 in which a nanopore 101 is formed, a first liquid tank 104A, a second liquid tank 104B, a first electrode 105A, and a second electrode 105B. The first liquid tank 104A and the second liquid tank 104B are disposed so as to be in contact with the thin film 102 interposed therebetween. The first liquid tank 104A and the second liquid tank 104B are filled with an electrolyte solution 103. The first electrode 105A is provided in the first liquid tank 104A. The second electrode 105B is provided in the second liquid tank 104B.

The nanopore device 100 can be formed, for example, by holding the thin film 102 by a flow cell. The nanopore device 100 of FIG. 2 is in a state where the nanopore 101 is formed in the thin film 102 and a biopolymer 109 (DNA chain or the like) is introduced. In order to control the biopolymer 109 at an optional speed, a molecular motor 110 made of, for example, an enzyme such as polymerase is provided at one end of the biopolymer 109.

It is only necessary that the biopolymer 109 is an object to be measured which changes electrical characteristics, in particular, a resistance value, when passing through the nanopore. Typical examples thereof include nucleic acids such as single-stranded DNA, double-stranded DNA, RNA, PNA (peptide nucleic acid), oligonucleotide, and a combination thereof (for example, hybrid nucleic acid). When the nanopore device 100 analyzes monomer sequence, the biopolymer 109 needs to take the form of a linear polymer having an eliminated higher order structure. It is possible to adopt transportation according to electrophoresis as means for causing the biopolymer 109 to pass through the nanopore 101 However, it may be a solvent flow generated by a pressure potential difference and the like.

The electrolyte solution 103 is the above-described pore forming solution or measurement solution. The volume of the electrolyte solution 103 is, for example, on the order of microliters or milliliters.

The power source 107 applies a predetermined voltage between the first electrode 105A and the second electrode 105B. When a voltage is applied between the first electrode 105A and the second electrode 105B, a potential difference occurs between both surfaces of the thin film 102 in which the nanopore 101 is formed. The biopolymer 109 dissolved in the first liquid tank 104A (cis tank) located on the upper side is migrated toward the second liquid tank 104B (trans tank) located on the lower side.

The ammeter 106 measures an ion current (blockade signal) flowing between the first electrode 105A and the second electrode 105B to output the measurement value to the computer 108. The ammeter 106 includes an amplifier that amplifies a current flowing between the electrodes by applying a voltage, and an analog to digital converter (ADC) (not illustrated). A detection value which is an output of the ADC is output to the computer 108.

The computer 108 controls voltages applied to the first electrode 105A and the second electrode 105B by the power source 107. The computer 108 analyzes the biopolymer 109 based on the detection value of the current from the ammeter 106. More specifically, the computer 108 obtains the sequence information of the biopolymer 109 based on the value of the ion current (blockade signal).

As the nanopore measurement method, the following methods can also be adopted in addition to the method for measuring the blockade current as described above. One of the methods is a method for providing another pair of electrodes in the vicinity of the nanopore in addition to the first electrode 105A and the second electrode 105B, applying a voltage between the pair of electrodes, and measuring a change of a tunnel current generated when the biomolecule passes. In addition, there is a method for providing an FET device on a nanopore membrane and measuring a signal change of a transistor obtained by the device. It is also possible to measure optical signals such as absorption, reflection, or fluorescence characteristics of light emitted to the vicinity of the nanopore.

Typically, the computer 108 includes an ionic current measurement device, an analog digital output conversion device, a data processing device, a data display output device, and an input/output auxiliary device. The ionic current measurement device is equipped with a current-voltage converting type high-speed amplifying circuit. The data processing device is equipped with an arithmetic device, a temporary storage device, and a non-volatile storage device. By covering the nanopore device 100 with a Faraday cage, external noise can be reduced.

As shown in FIG. 2, the ammeter 106, the power source 107, and the computer 108 may not be separate members from the pore device 100, but may be integrated with the nanopore device 100.

Hereinafter, a method for producing the above-described biomolecule analysis device 1 will be described. The basic configuration itself of the biomolecule analysis device used for analyzing the biomolecule with the so-called blockade current method is known in the art. The components thereof can also be easily understood by those skilled in the art. For example, specific devices are disclosed in U.S. Pat. No. 5,795,782, "Scientific Reports 4, 5000, 2014, Yanagi et al.", "Nanotechnology 25 275501, 2014, Akahori et al.", "Scientific Reports, 5, 14656, 2015, Yanagi et al.", and "Scientific Reports 5, 16640, 2015, Goto et al."

The thin film 102 in which the nanopore 101 is formed may be a lipid bilayer (biopore) composed of an amphipathic molecular layer in which a protein having a pore at its center is embedded, or may be a thin film (solid pore) composed of a material that can be formed by a semiconductor microfabrication technique. Examples of the material which can be formed by the semiconductor microfabrication technique include silicon nitride (SiN), silicon oxide ($SiO_2$), silicon oxynitride (SiON), hafnium oxide ($HfO_2$), molybdenum disulfide ($MoS_2$), and graphene. The thickness of the thin film 102 may be 1 Å (angstrom) to 200 nm, optionally 1 Å to 100 nm or 1 Å to 50 nm in accordance with some situation, and specifically, for example, about 5 nm.

The area of the thin film 102 may be set to a size with which it is difficult to form two or more nanopores 101 when forming the nanopores 101 by applying a voltage and a size with which allowable strength is provided. As an example, the area may be, for example, about 100 to 500 nm. By setting the film thickness of the thin film 102 to a film thickness capable of forming the nanopore 101 having an effective film thickness equivalent to a single base, single-base resolution of DNA can be achieved. As an example, the film thickness can be set to about 7 nm or less. The thin film 102 may have a structure in which both surfaces are held by another thin film having a through hole. In this case, the area of the thin film 102 exposed by the through holes on both surfaces may be set as described above.

As the dimension (diameter) of the nanopore 101, an appropriate dimension can be selected according to the type of the biopolymer 109 to be analyzed. As an example, the dimension of the nanopore 101 can be set to, for example, 0.9 nm to 100 nm, and optionally 0.9 nm to 50 nm in accordance with some situation. When single-stranded DNA is an object to be measured as the biopolymer 109, the diameter can be set such that the single-stranded DNA can pass, and can be specifically set to about 0.9 nm or more and 10 nm or less. For example, the diameter of the nanopore 101 used for analysis of ssDNA (single-stranded DNA) having a diameter of about 1.4 nm can be set to 1.4 nm to 10 nm, and can be optionally set to about 1.4 nm to 2.5 nm, specifically about 1.6 nm in accordance with some situation.

For example, the diameter of the nanopore 101 used for analysis of dsDNA (double-stranded DNA) having a diameter of about 2.6 nm can be set to about 3 nm to 10 nm, and can be optionally set to about 3 nm to 5 nm in accordance with some situation.

The depth of the nanopore 101 can be adjusted by adjusting the thickness of the thin film 102. The depth of the nanopore 101 may be twice or more of a monomer unit constituting the biopolymer 109. The depth of the nanopore 101 may be optionally three times or more or five times or more of the size of the monomer unit in accordance with some situation. For example, when the biopolymer 109 is composed of a nucleic acid, the depth of the nanopore 101 can be set to the size of three or more bases, for example, about 1 nm or more. This allows the biopolymer 109 to enter the nanopore 101 while controlling its shape and movement speed, thereby enabling analysis with high sensitivity and high accuracy. The shape of the nanopore 101 is basically a circle, but may be an oval shape or a polygonal shape.

In the case of an array type device configuration including a plurality of thin films 102 having nanopores 101, it is preferable that the thin films 102 having nanopores 101 are regularly arranged. The interval at which the plurality of thin films 102 are disposed can be set to 0.1 μm to 1 mm or 1 μm to 700 μm, depending on the electrode to be used and the capability of an electric measurement system.

Meanwhile, the method for forming the nanopore 101 in the thin film 102 is not particularly limited. For example, it is possible to use electron beam irradiation from a transmission electron microscope (TEM) or the like, or dielectric breakdown from application of a voltage (pulse voltage or the like) or the like. As the method for forming the nanopore 101, for example, it is possible to use the methods described in "Itaru Yanagi et al., Scientific Reports 4, 5000 2014, Yanagi et al." and "A. J. Storm et al., Nat. Mat. 2 537 (2003)."

When a voltage is applied from the power source to the electrodes provided in the two upper and lower liquid tanks, an electric field is generated in the vicinity of the nanopore. The biopolymer that is negatively charged in the liquid passes through the nanopore. At that time, the above-described blockade current Ib flows.

It is possible to appropriately prepare the first liquid tank 104A and the second liquid tank 104B that can store the measurement solution coming into contact with the thin film 102, with a material, a shape, and a size that do not affect the measurement of the blockade current. The measurement solution is injected so as to come into contact with the thin film 102 that partitions the first liquid tank 104A and the second liquid tank 104B.

The first electrode 105A and the second electrode 105B can be made of a material capable of causing an electron transfer reaction (Faraday reaction) with the electrolyte in the measurement solution, and are typically made of silver halide or alkali silver halide. Silver or silver/silver chloride can be used from the viewpoint of potential stability and reliability.

The first electrode 105A and the second electrode 105B may be made of a material that serves as a polarization electrode, and may be made of, for example, gold or platinum. In this case, a substance capable of assisting an electron transfer reaction, for example, potassium ferricyanide or potassium ferrocyanide, can be added to the measurement solution in order to secure a stable ionic current. Alternatively, a substance capable of performing an electron transfer reaction, such as ferrocenes, can also be immobilized on the surface of the polarization electrode.

The structures of the first electrode 105A and the second electrode 105B may be entirely made of the above-described material, or the surface of a base material (copper or aluminum or the like) may be coated with the above-described material. The shapes of the first electrode 105A and the second electrode 105B are not particularly limited, but a shape having a large surface area in contact with the measurement solution can be adopted. The first electrode 105A and the second electrode 105B are joined to the wiring. Then, an electrical signal is transmitted to a measurement circuit (ammeter 106).

The biomolecule analysis device 1 includes the above components as elements. The above-described nanopore-type biomolecule analysis device 1 can be provided together with a manual describing the procedure and amount of use, and the like. A control strand used together with the molecular motor 110 may be provided in a ready-to-use state, or may be configured and provided in a state where only the biopolymer to be measured is not bonded. Such forms and preparations can be understood by those skilled in the art. Similarly, the nanopore device 100 may be provided in a state where the nanopore is formed in a ready-to-use state, or may be provided in a state where the nanopore is formed in a providing destination.

(Conclusion)

As described above, in the biomolecule analysis device according to the present embodiment, the electrolyte solution enclosed on both sides of the thin film contains the ammonium ions as the cations and the sulfate ions as the anions. The use of such a biomolecule analysis device allows to prevent the RTN with respect to the baseline current and the noise derived from the substrate contained in the measurement solution and allows to smoothly and correctly measure the blockade current in the nanopore.

In the nanopore device 100 of the biomolecule analysis device 1 exemplified in FIG. 2, one thin film 102 includes only one nanopore 101. However, this is merely an example, and it is also possible to provide an array device configured by forming a plurality of nanopores 101 in the thin film 102 and separating regions of the plurality of nanopores 101 by partition walls. Therefore, a configuration example of the array device will be described below.

Figure 3:
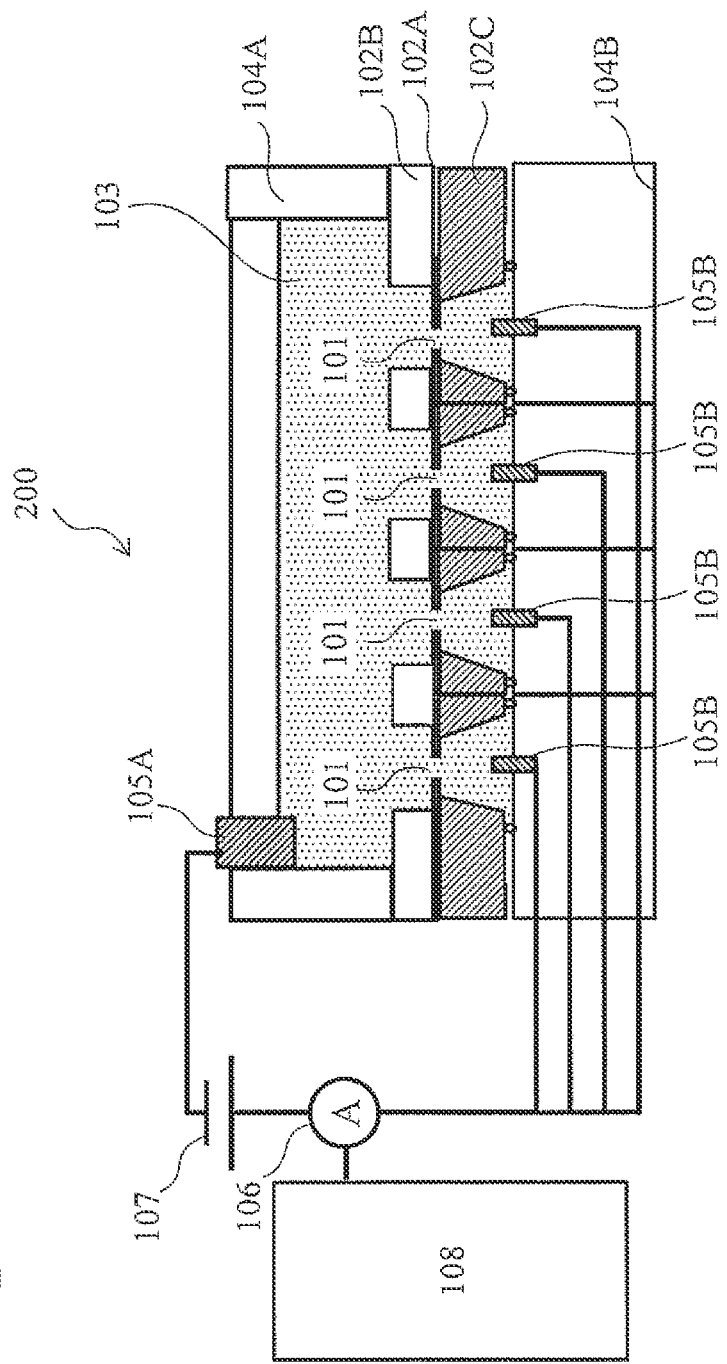
FIG. 3 is a schematic cross-sectional view showing another configuration of the biomolecule analysis device.

FIG. 3 is a schematic cross-sectional view showing the configuration of a biomolecule analysis device 2. In FIG. 3, the same components as those in the biomolecule analysis device 1 shown in FIG. 2 are denoted by the same reference numerals, and redundant description will be omitted. As shown in FIG. 3, the biomolecule analysis device 2 is different from the biomolecule analysis device 1 of FIG. 2 in that the biomolecule analysis device 2 includes a nanopore device 200 which is an array device.

In the nanopore device 200, a thin film 102A has a plurality of nanopores 101, and a second liquid tank 104B below the thin film 102A is divided into a plurality of spaces by partition walls (specifically, side walls of a thin film 102C). In the thin films 102B and 102C for fixing the thin film 102A, through holes are provided at positions corresponding to the nanopores 101. The plurality of spaces (individual tanks) are formed by side walls of the through holes of the thin film 102C. A second electrode 105B is provided in each of the plurality of spaces. A first liquid tank 104A is used as a common liquid tank for the plurality of spaces located on the lower side. The plurality of spaces are insulated from each other by partition walls. Therefore, it is possible to independently measure the current flowing through each nanopore 101.

The above-described solution may be used as a nanopore forming solution or a measurement solution (electrolyte solution 103). As a result, an effect of suppressing RTN noise superimposed on a baseline current and noise derived from a substrate is exerted. The biomolecule analysis device 2 can perform measurements in parallel, so that the monomer sequence of the biopolymer can be analyzed with very high throughput while high analysis accuracy is maintained.

The biomolecule analysis method, the biomolecule analyzing reagent, and the biomolecule analysis device according to the present disclosure are useful, for example, in the field of analysis of a biopolymer composed of a nucleic acid, and in the fields of test, diagnosis, therapy, drug discovery, and fundamental research and the like utilizing the analysis.

EXAMPLES

Hereinafter, the technique of the present disclosure will be described in more detail by way of Examples. However, the technique of the present disclosure is not limited to these Examples.

[Preparation of Biomolecule Analysis Device]

In the following Examples, a single-pore biomolecule analysis device having a configuration shown in FIG. 2 is used. First, a nanopore device was produced as follows.

According to the following procedure, a thin film was produced by a semiconductor microfabrication technique. First, $Si_3N_4$, polySi, and $Si_3N_4$ were formed in the order of film thicknesses of 5 nm, 150 nm, and 100 nm on the front surface of an 8 inch Si wafer having a thickness of 725 mm. $Si_3N_4$ was formed at 105 nm on the back surface of the Si wafer. The polySi as the intermediate layer may be SiO.

Then, the $Si_3N_4$ at the top of the front surface of the Si wafer was removed by reactive ion etching in 500 nm square. Similarly, the $Si_3N_4$ on the back surface of the Si wafer was removed by reactive ion etching in 1038 μm square. The back surface of a Si substrate exposed by etching was further etched with tetramethylammonium hydroxide (TMAH). During Si etching, the surface of the wafer was covered with a protective film (ProTEK (registered trademark) B3 primer and ProTEK (registered trademark) B3, manufactured by Brewer Science, Inc.) in order to prevent etching of polySi on the front surface side.

Then, after the protective film was removed, the polySi layer exposed in 500 nm square was removed with an $NH_4OH$ solution. Thus, a partition body was obtained in which the $Si_3N_4$ thin film having a film thickness of 5 nm was exposed. When SiO is selected for a sacrificial layer, the thin film is exposed by etching with a BHF solution (HF: NH$_4$F=1:60). At this stage, the nanopore is not provided in the thin film.

The nanopore was formed by the following procedure. Before the partition body was set in a biomolecule analysis device or the like, the Si$_3$N$_4$ thin film was hydrophilized by immersing the partition body in a piranha solution (H$_2$SO$_4$: H$_2$O$_2$=3:1) for 3 minutes. After the immersion, the partition body was washed under running pure water for 5 minutes or more. The hydrophilization can also be performed under conditions of 10 W, 20 sccm, 20 Pa, and 45 sec by Ar/O$_2$ plasma (manufactured by Samco Inc.). Then, the partition body was set in the biomolecule analysis device. Thereafter, upper and lower liquid tanks sandwiching the thin film were filled with a nanopore forming solution. An electrode was introduced into each of the liquid tanks. As the electrode, a silver/silver chloride electrode was used. Water was used as a solvent of the nanopore forming solution.

The voltage is applied not only when the nanopore is formed, but also when the ionic current flowing through the nanopore is measured after the nanopore is formed. Here, the liquid tank located on the lower side is referred to as cis tank, and the liquid tank located on the upper side is referred to as trans tank. A voltage Vcis applied to the electrode on the cis tank side is set to 0 V. A voltage Vtrans is applied to the electrode on the trans tank side. The voltage Vtrans is generated by a pulse generator (for example, 41501B SMU AND Pulse Generator Expander, manufactured by Agilent Technologies, Inc.).

The current value after pulse application can be read by an ammeter (for example, 4156B PRECISION SEMICONDUCTOR ANALYZER, manufactured by Agilent Technologies, Inc.). A current value condition (threshold current) can be selected in accordance with the diameter of the nanopore formed before the application of the pulse voltage. The desired diameter can be obtained while the diameter of the nanopore is sequentially increased.

The diameter of the nanopore can be estimated from the ion current value. Condition selection criteria are as shown in Table 1.

TABLE 1

| | voltage application conditions | | |
|---|---|---|---|
| Diameter of nanopore before application of pulse voltage | Non-opening to Φ 0.7 nm | Non-opening to Φ 1.4 nm | Non-opening to Φ 1.5 nm |
| Applied voltage (V$_{cis}$) [V] | 5 | 3 | 2.5 |
| Initial application time [s] | 0.01 | 0.01 | 0.001 |
| Threshold current | 0.2 nA/0.4 V | 0.5 nA/0.1 V | 0.6 nA/0.1 V |

Here, the n-th pulse voltage application time $t_n$ (where n is an integer of 2 or more) is determined by the following expression.

$$t_n = 10^{-3+(1/6)(n-1)} - 10^{-3+(1/6)(n-2)} \text{ For } n>2 \quad \text{[Equation 1]}$$

Experimental Example 1: Change of Measurement Solution

Example 1

In Example 1, a nanopore was formed using a 1 M CaCl$_2$+10 mM Tris solution (pH 7.5) as a nanopore forming solution. Thereafter, the nanopore forming solution was discharged, and replaced with a 0.5 M (NH$_4$)$_2$SO$_4$+0.5 M KCl+10 mM Tris solution (pH 7.5) as a measurement solution. After the replacement with the measurement solution, the time change of a baseline current was measured. Thereafter, ssDNA (polyT 60mer) was added to measure the temporal change of an ion current.

Comparative Example 1

In Comparative Example 1, the time change of a baseline current and the time change of an ion current after the addition of ssDNA (polyT 60mer) were measured in the same manner as in Example 1 except that a 1 M KCl+1×TE solution was used as a measurement solution.
(Results)

Figure 4A:
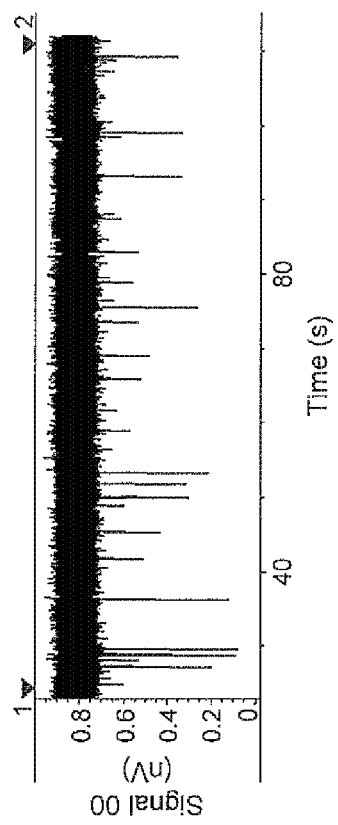
FIGS. 4A-4D are graphs showing the result of Experimental Example 1.
Figure 4B:
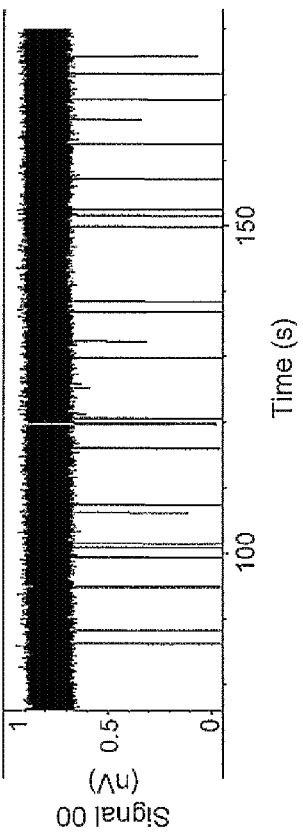
Figure 4C:
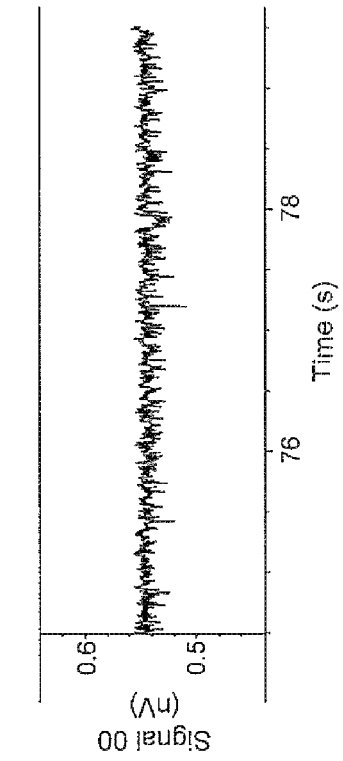
Figure 4D:
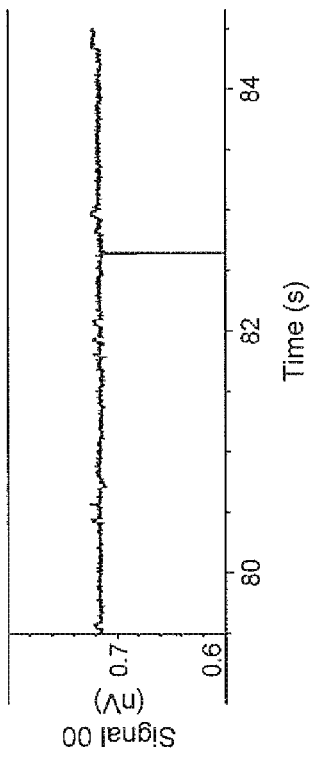

FIGS. 4A-4D are graphs showing the result of Experimental Example 1. FIG. 4A) shows a baseline current before the addition of ssDNA in Comparative Example 1. FIG. 4B shows an ion current after the addition of ssDNA in Comparative Example 1. FIG. 4c shows a baseline current before the addition of ssDNA in Example 1 FIG. 4D shows an ion current after the addition of ssDNA in Example 1.

As shown in FIGS. 4A and 4C, in Comparative Example 1, baseline noise in the case of the replacement with the KCl solution was Irms=4.68 pA (LPF 100 Hz), whereas in Example 1, baseline noise in the case of the replacement with the (NH$_4$)$_2$SO$_4$ mixed solution was reduced to Irms=1.22 pA (LPF 100 Hz).

As shown in FIGS. 4A and 4D, the amount of a blockade signal derived from ssDNA obtained in the (NH$_4$)$_2$SO$_4$ mixed solution in Example 1 became uniform such that a peak could be confirmed in the histogram distribution of a blockade amount as compared with the amount of a blockade signal derived from SSDNA obtained in the KCl solution in Comparative Example 1.

Experimental Example 2: Change of Nanopore Forming Solution

Example 2

In Example 2, a nanopore was formed using a 0.5 M (NH$_4$)$_2$SO$_4$ solution as a nanopore forming solution. Here, the time change of a baseline current was measured without replacement with another solution. Thereafter, the nanopore forming solution was discharged, and replaced with a 1 M KCl solution as a measurement solution. After the replacement with the measurement solution, the time change of a baseline current was measured.

Comparative Example 2

In Comparative Example 2, a nanopore was formed using a 1 M CaCl$_2$)+10 mM Tris solution (pH 7.5). Thereafter, the nanopore forming solution was discharged, and replaced with a 1 M KCl solution as a measurement solution. After the replacement with the measurement solution, the time change of a baseline current was measured.
(Results)

Figure 5A:
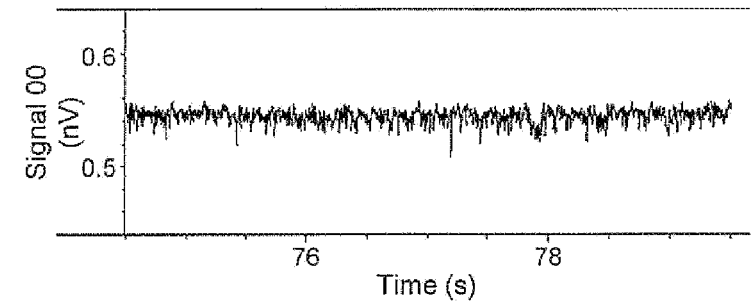
FIGS. 5A-5C are graphs showing the result of Experimental Example 2.
Figure 5B:
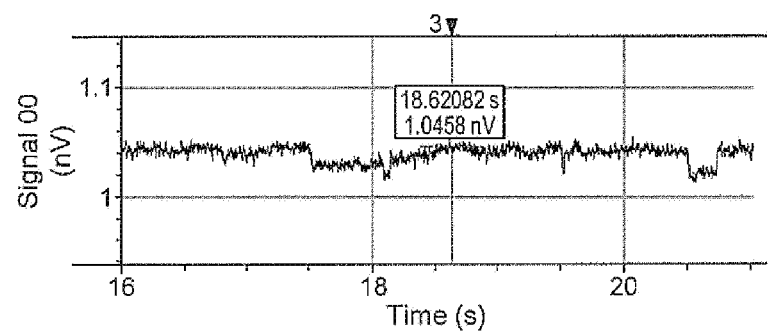
Figure 5C:
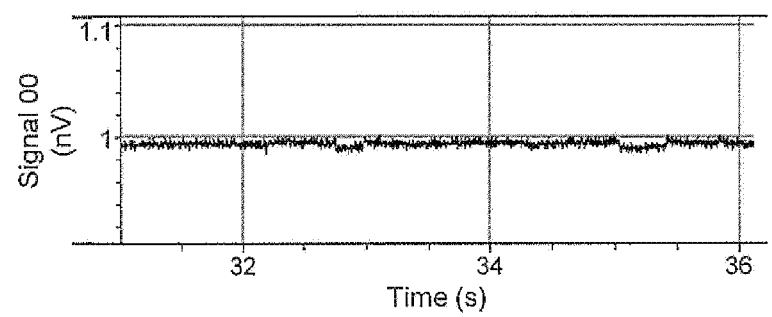

FIGS. 5A-5C are graphs showing the result of Experimental Example 2. FIG. 5A shows a baseline current in Comparative Example 2. FIG. 5B shows a baseline current after replacement with a 1M KCl solution in Example 2. As shown in FIGS. 5A and 5B, in Comparative Example 2, baseline current noise when a nanopore was formed with a CaCl$_2$ solution was Irms=4.68 pA, whereas in Example 2, baseline noise when a pore was formed with a 0.5 M $(NH_4)_2SO_4$ solution was reduced to Irms=3.13 pA. From this, it is found that the effect of Example 1 described above can be confirmed even when an ammonium sulfate-added solution is used for an electrolyte used during the formation of a pore due to dielectric breakdown.

FIG. 5C shows a baseline current measured without replacement of the solution after the formation of the nanopore in Example 2. It is found that baseline noise at this time is Irms=2.62 pA, and is further reduced as compared with the case of FIG. 5B.

From the results of Experimental Examples 1 and 2 described above, it was confirmed that RTN during the measurement of an ion current could be suppressed by using the solution containing $(NH_4)_2SO_4$ during the formation of the nanopore due to dielectric breakdown and/or during the measurement of the ion current.

Experimental Example 3: Introduction of Substrate

When the base sequence of DNA is analyzed by the ion current, it is necessary to suppress the passage rate of the DNA through the nanopore to be equal to or less than the response rate of an amplifier. One of the realization means is, for example, to transport the DNA in the vicinity of the nanopore using polymerase which is one of molecular motors. The polymerase requires a substrate for transporting the DNA. The substrate is deoxynucleoside triphosphates (dNTP) or the like. In the analysis using the nanopore device, the driving of the polymerase is achieved by dissolving the dNTP in the electrolyte in the cis tank. However, since this substrate is negatively charged, the substrate can pass through the nanopore. Since the minute pore is formed for decoding the sequence of the biopolymer, the substrate can also be obtained as a signal.

Therefore, in this Experimental Example, measured is a baseline current when a buffer and a substrate for driving the polymerase are mixed into the measurement solution.

Example 3

In each of the three nanopore devices (devices 1 to 3) produced under the above conditions, after a nanopore was formed, the time change of a baseline current was measured using a 0.5 M $(NH_4)_2SO_4$+0.5 M KCl+1×buffer+100 μM dNTP solution as a measurement solution. In the case where the concentration of dNTP was 1 mM, the time change of a baseline current was similarly measured.

Comparative Example 3

After a nanopore was formed, the time change of a baseline current was measured using a 1 M KCl+1×buffer+10 mM $MgCl_2$+100 μM dNTP solution as a measurement solution. In the case where the concentration of KCl was 3 M, the time change of a baseline current was similarly measured.
(Results)

FIGS. 6A-6C are graphs showing the result of Experimental Example 3. FIG. 6A) shows a baseline current in Comparative Example 3. As shown in FIG. 6A, a resistance component of about 100 to 200 pA is added to a pore current and is also superimposed on a blockade signal.

FIG. 6B shows a baseline current when the dNTP concentration is 100 μM in Example 3. As shown in FIG. 6B, it is found that noise derived from a substrate superimposed on a baseline is reduced as compared with FIG. 6A. In FIG. 6B, the noise of the baseline current was 24 pA (LPF 1 kHz) on average.

FIG. 6C shows a baseline current when the dNTP concentration is 1 mM in Example 3. As shown in FIG. 6C, it was found that even when the concentration of the substrate was 1 mM, a noise level was about 50 pA and was suppressed by about 30% with respect to a noise level of Comparative Example 3.

Experimental Example 4: Confirmation of Activity of Molecular Motor

In the present Experimental Example, confirmed is the extension reaction activity of polymerase in a measurement solution having a liquid temperature of 37° C.

Example 4

100 μM dNTP and 0.1 M, 0.2 M, 0.3 M, 0.4 M or 0.5 M $(NH_4)_2SO_4$ were added to 1×DNA polymerase buffer to prepare a measurement solution. A mold/primer concentration was 250 nM.

Comparative Example 4

In place of $(NH_4)_2SO_4$ in Example 4, 0.15 M, 0.2 M, 0.3 M, 0.5 M, or 1 M KCl was used as a measurement solution.
(Confirmation of Activity)

In order to detect the activity of enzyme, first, in an isothermal amplification process, the reaction rate of the enzyme was obtained from the time dependence of fluorescence intensity incorporated with the extension of DNA, and the dependence on the amount of the enzyme added was obtained.

Figure 7C:
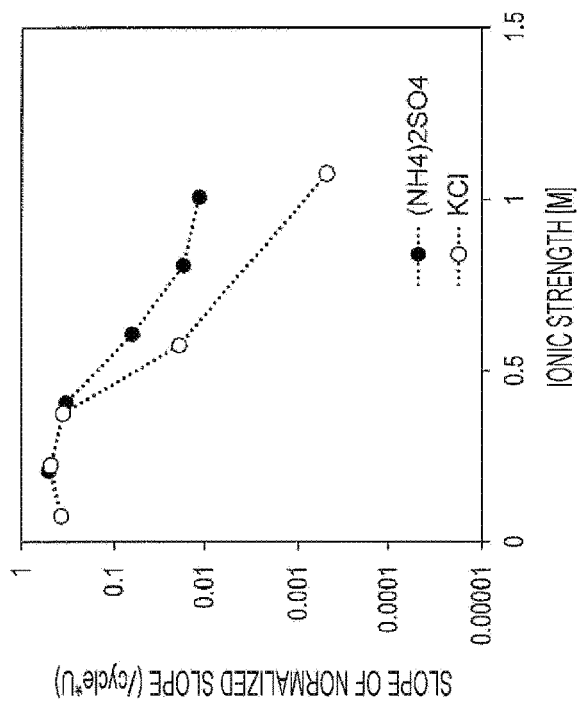
FIGS. 7A-7C are graphs showing the result of Experimental Example 4.
Figure 7A:
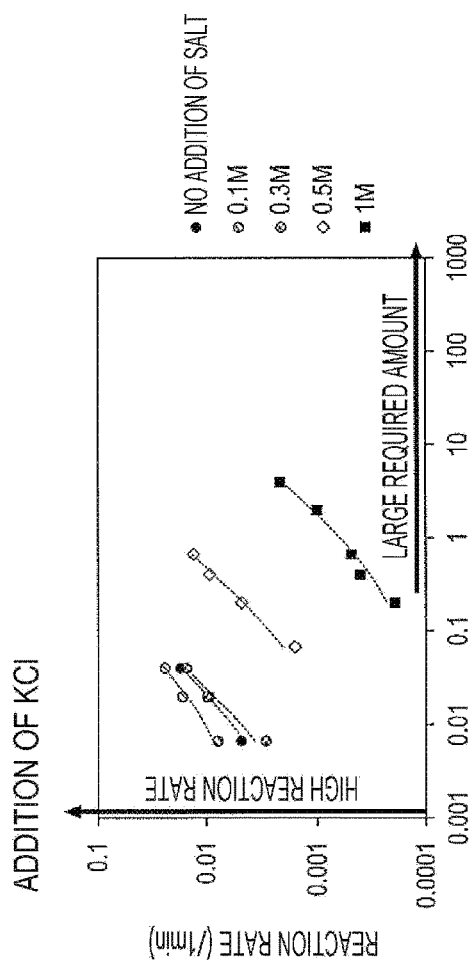
Figure 7B:
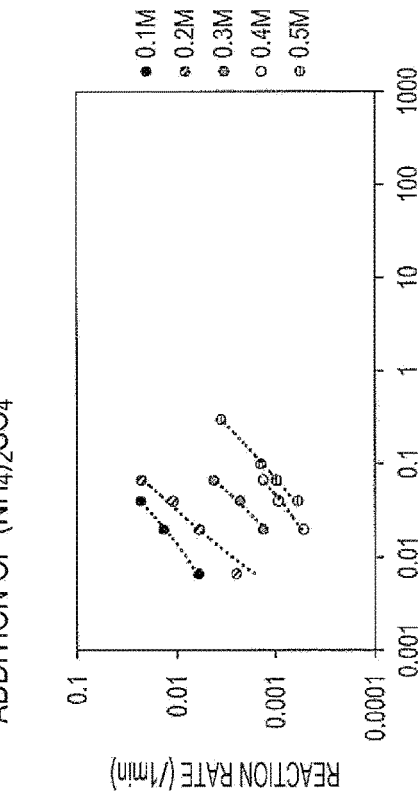

FIG. 7A shows a fluorescence intensity increase rate according to the amount of the enzyme added, that is, a change of the reaction rate (/time) when the salt concentration of KCl (Comparative Example 4) is changed. FIG. 7B shows a fluorescence intensity increase rate according to the amount of the enzyme added, that is, a change of the reaction rate (/time) when the salt concentration of $(NH_4)_2SO_4$ (Example 4) is changed. As the amount of the enzyme added increases, the reaction rate increases, so that each condition is upward to the right.

Here, when the concentration of the added salt increases, the enzyme activity of one molecule decreases. Thus, a time required to obtain the same DNA length increases. Since a deactivation rate in an enzyme population also increases at the time, the required amount of the enzyme added also tends to increase.

As described above, typically, it can be considered that as the inclinations in FIGS. 7A and 7B are greater, the enzyme activity is higher, and as the inclinations are lower, the enzyme activity is lower. Therefore, in order to compare the activities of the enzyme in salt species and salt concentrations, the slopes of the graphs in the salt species and the salt concentrations obtained in FIGS. 7A and 7B are determined as normalized slopes.

FIG. 7C is a graph obtained by plotting a normalized slope according to the ionic strength of the used solution. Since the ionic strength of a buffer is 0.075 M, the ionic strength is added to the concentration of an electrolyte at each point. In the case of $(NH_4)_2SO_4$, two times of the salt concentration is regarded as the ionic strength, and then, a normalized slope is plotted.

From FIG. 7C, it was found that in $(NH_4)_2SO_4$ (Example 4), the activity did not change up to the ionic strength of 0.5 M as compared with the case where no salt was added. This means that in the case of KCl (Comparative Example 4) that has been conventionally used, the activity does not change up to the ionic strength of 0.3 M, but more salt can be added. This is also useful knowledge in securing SN in ion current measurement using a nanopore.

Experimental Example 5: Changes in Addition Amount and Addition Rate of Ammonium Sulfate In the present Experimental Example, confirmed is a change of a noise reduction effect when the addition amount and the addition rate of $(NH_4)_2SO_4$ are changed.

Example 5

In Example 5, only $(NH_4)_2SO_4$ was used as an electrolyte (salt), and measurement solutions (the ratio of ammonium sulfate was 100%) having total salt concentrations of 0.2 M and 0.05 M were prepared. A 0.05 M $(NH_4)_2SO_4$+0.15 M KCl solution (the ratio of ammonium sulfate: 25%) and a 0.012 M $(NH_4)_2SO_4$+0.188 M KCl solution (the ratio of ammonium sulfate: 6%) were prepared with the total salt concentration set to 0.2 M.

A nanopore was formed by using a $CaCl_2$) solution as a nanopore forming solution. Then, the nanopore forming solution was replaced respectively with the measurement solutions in which the ratio of the concentration of the ammonium sulfate to the total salt concentration was 100% (0.2 M and 0.05 M), the measurement solutions in which the ratio of the concentration of the ammonium sulfate to the total salt concentration was 25%, and the measurement solutions in which the ratio of the concentration of the ammonium sulfate to the total salt concentration was 6%, to measure the time change of a baseline current.

Comparative Example 5

In Comparative Example 5, a nanopore was formed by using a $CaCl_2$) solution as a nanopore forming solution. The solution was then replaced with a 1 M KCl solution to measure the time change of a baseline current.
(Results)
FIGS. 8A and 8B are graphs showing the result of Experimental Example 5. FIG. 8A shows the result of Comparative Example 5. FIG. 8B shows the result of Example 5.

As shown in FIG. 8B, it was found that the salt concentration of $(NH_4)_2SO_4$ decreased to increase noise. It is found that the concentration of $(NH_4)_2SO_4$ is 0.05 M or more to provide a high noise reduction effect. Even at the same $(NH_4)_2SO_4$ concentration, a clear increase in a noise amount due to the presence of KCl is not confirmed. It is found that the noise reduction effect is high when the ratio of $(NH_4)_2SO_4$ to the total concentration of salts is 25% or more.

Experimental Example 6: Changes in Addition Amount and Addition Rate of Ammonium Sulfate Upon Introduction of Substrate Example 6

In Example 6, 100 μM dNTP was added to each measurement solution of Example 5. The time change of a baseline current was measured in the same manner as in Example 5 except for the above.

Comparative Example 6

In Comparative Example 6, 100 mM dNTP was added to each measurement solution of Comparative Example 5. The time change of a baseline current was measured in the same manner as in Comparative Example 5 except for the above.
(Results)
FIGS. 9A and 9B are graphs showing the result of Experimental Example 6. FIG. 9A shows the result of Comparative Example 6. FIG. 9B shows the result of Example 6.

As shown in FIGS. 9A and 9B, it was confirmed that noise derived from the substrate was suppressed when the measurement solution contains $(NH_4)_2SO_4$ (Example 6) regardless of the salt addition amount and the salt addition rate. Based on the fact that the addition rate of $(NH_4)_2SO_4$ in FIG. 9A is less than 6%, it is found that a noise reduction effect is improved by adding at least 12 mM or more or 6% or more of $(NH_4)_2SO_4$.

Experimental Example 7: Formation of Nanopore in $(NH_4)_2SO_4$ Solution

Example 7

In Example 7, a nanopore was formed by dielectric breakdown using a 0.05 M $(NH_4)_2SO_4$+0.15 M KCl solution (the ratio of ammonium sulfate was 25%) as a nanopore forming solution. Thereafter, a measurement solution was replaced with a 1M KCl solution and then the time change of a baseline current was measured. Similarly, when the measurement solution was replaced with a 1 M KCl+100 mM dNTP solution, the time change of a baseline current was measured.

Figure 10:
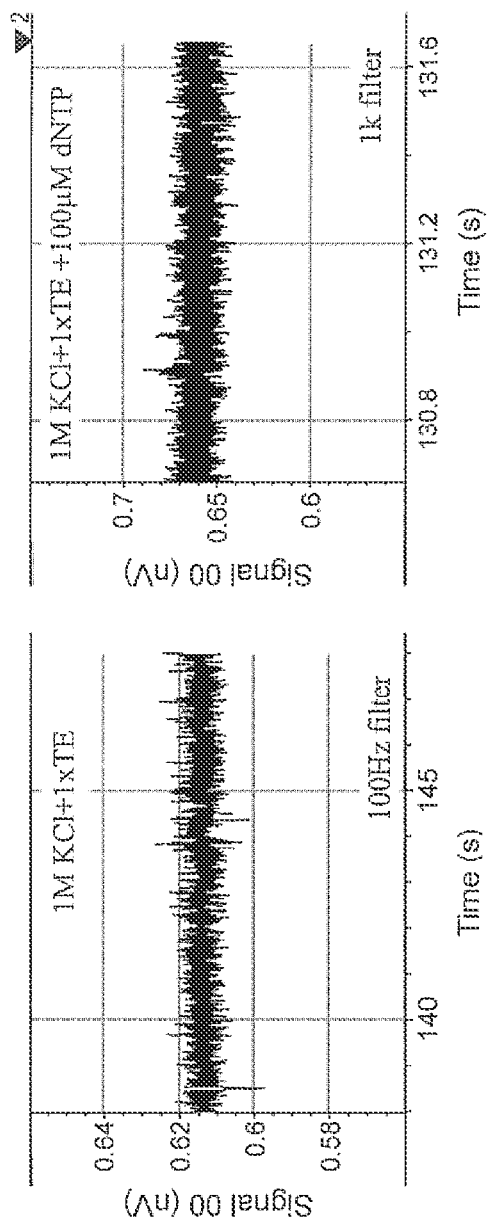
FIG. 10 is a graph showing the result of Experimental Example 7.

FIG. 10 is a graph showing the result of Experimental Example 7. As shown in the left diagram of FIG. 10, it was found that when the nanopore was formed in the $(NH_4)_2SO_4$ solution and the solution is then replaced with a 1 M KCl solution, the amount of noise is 35.7 pA and the noise can be sufficiently suppressed. As shown in the right diagram of FIG. 10, it was found that noise derived from dNTP can be suppressed even when the solution was replaced with a solution containing dNTP. Therefore, it is found that a noise reduction effect is expected by using the ammonium sulfate-added solution having at least an addition rate of 25% as a nanopore forming reagent used upon dielectric breakdown.

Experimental Example 8: Change of Electrolyte

In the above Experimental Examples, ammonium sulfate was used as an electrolyte (salt) that generated ammonium ions and sulfate ions. Meanwhile, in the present Experimental Example 8, ammonium chloride is used as an ammonium ion source, and magnesium sulfate is used as a sulfate ion source.

Reference Example 1

In Reference Example 1, a nanopore was formed using a 1 M $CaCl_2$)+10 mM Tris solution (pH 7.5) as a nanopore forming solution. Thereafter, the nanopore forming solution was discharged and replaced with a 0.2 M $MgSO_4$ solution as a measurement solution. After the replacement with the measurement solution, the time change of a baseline current was measured. Similarly, when the measurement solution was replaced with a 0.2 M NH$_4$Cl solution, the time change of a baseline current was measured.

Comparative Example 8

Figure 11A:
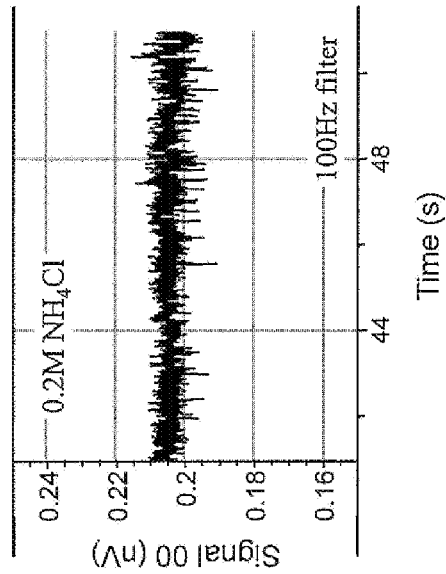
FIGS. 11A-11C are graphs showing the result of Experimental Example 8.
Figure 11B:
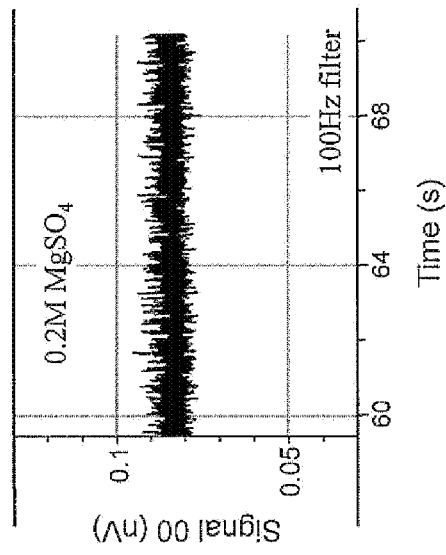
Figure 11C:
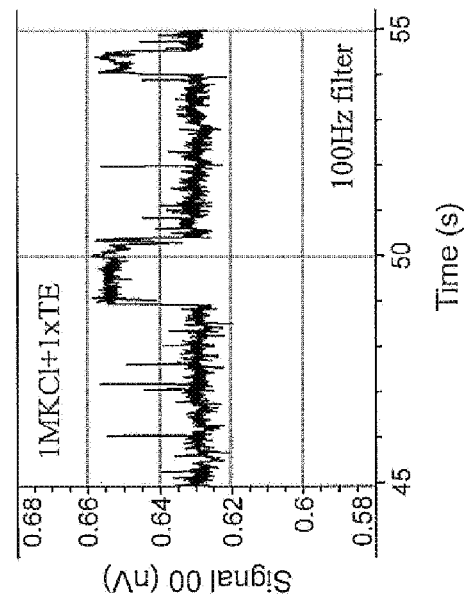

In Comparative Example 8, the time change of a baseline current was measured in the same manner as in Example 8 except that a 1M KCl+1×TE solution was used as a measurement solution.
(Results)
FIGS. 11A-11C are graphs showing the result of Experimental Example 8. FIG. 11A shows a baseline current when a 0.2 M MgSO$_4$ solution is used. FIG. 11B shows a baseline current when a 0.2 M NH$_4$Cl solution is used. FIG. 11C shows a baseline current when a KCl solution is used. As shown in FIGS. 11A-11C, it is found that the noise of the baseline current in the case of the solution containing either sulfate ions or ammonium ions (Reference Example 1) is smaller than that in the case of the solution not containing these ions (Comparative Example 8).

Experimental Example 9: Introduction of Substrate

Reference Example 2

In Reference Example 2, 100 μM dNTP was added to each of the measurement solutions of Reference Example 1. The time change of a baseline current was measured in the same manner as in Reference Example 1 except for the above.

Comparative Example 9

Figure 12B:
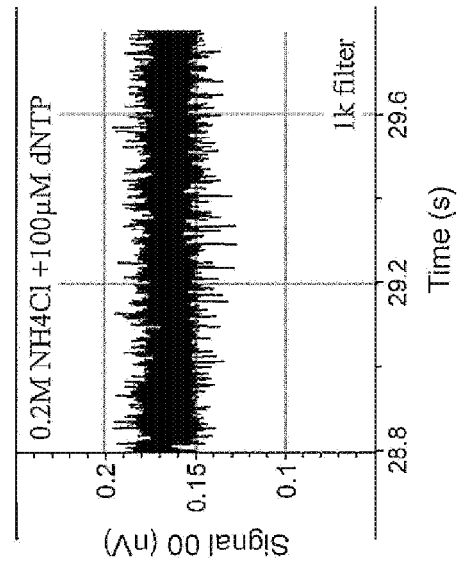
FIGS. 12A-12C are graphs showing the result of Experimental Example 9.
Figure 12A:
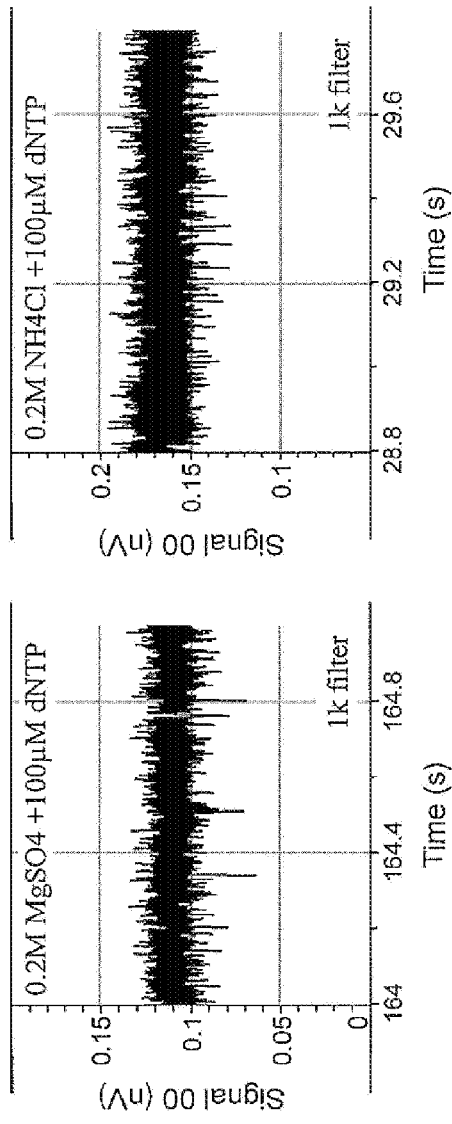
Figure 12C:
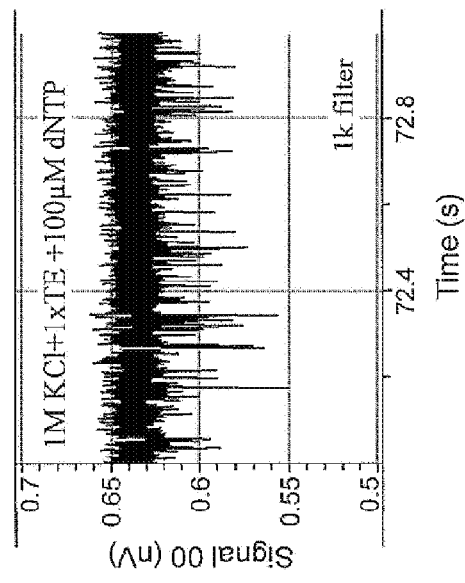

In Comparative Example 9, the time change of a baseline current was measured in the same manner as in Comparative Example 8 except that 100 μM dNTP was added to the measurement solution of Comparative Example 8.
(Results)
FIGS. 12A-12C are graphs showing the result of Experimental Example 9. FIG. 12A shows a baseline current when a 0.2 M MgSO$_4$+100 μM dNTP solution is used. FIG. 12B shows a baseline current when a 0.2 M NH$_4$Cl+100 μM dNTP solution is used. FIG. 12C shows a baseline current when a KCl+100 μM dNTP solution is used. As shown in FIGS. 12A-12C, it is found that the noise of the baseline current in the case of the solution containing either sulfate ions or ammonium ions (Reference Example 2) is smaller than that in the case of the solution not containing these ions (Comparative Example 9) even if the substrate is mixed.

MODIFICATION EXAMPLES

The present disclosure is not limited to the above-described embodiments and so it includes various modification examples. For example, the above-described embodiments have been described in detail to clearly describe the present disclosure. The present invention need not necessarily include all the described configurations. A part of one embodiment can be replaced by the configuration of another embodiment. The configuration of another embodiment can also be added to the configuration of one embodiment. It is also possible to, for a part of the configuration of each embodiment, add, delete, or replace a part of the configuration of another embodiment.

All the publications and patent applications cited herein are incorporated herein by reference as it is.

REFERENCE SIGNS LIST 1, 2 biomolecule analysis device
100, 200 nanopore device
101 nanopore
102 thin film
103 electrolyte solution
104A first liquid tank
104B second liquid tank
105A first electrode
105B second electrode
106 ammeter
107 power source
108 computer
109 biopolymer
110 molecular motor

The invention claimed is:

1. A biomolecule analysis method comprising:
preparing a biomolecule analysis device including a thin film, a first liquid tank and a second liquid tank separated by the thin film, a first electrode disposed in the first liquid tank, and a second electrode disposed in the second liquid tank; and
forming a nanopore in the thin film by applying a first voltage between the first electrode and the second electrode in a state where a nanopore forming solution is enclosed in the first liquid tank and the second liquid tank,
wherein the nanopore forming solution contains ammonium ions and sulfate ions,
wherein the nanopore forming solution is an ammonium sulfate solution, and
wherein the ammonium sulfate solution has an ammonium sulfate concentration of 0.01 M or more to suppress a noise in a baseline current.

2. The biomolecule analysis method according to claim 1, further comprising measuring a current flowing between the first electrode and the second electrode by applying a second voltage between the first electrode and the second electrode in a state where a measurement solution is enclosed in the first liquid tank and the second liquid tank after formation of the nanopore,
wherein the measurement solution also contains the ammonium sulfate solution having an ammonium sulfate concentration of 0.01 M or more.

3. The biomolecule analysis method according to claim 1, wherein
the ammonium sulfate solution has an ammonium sulfate concentration of 0.01 M or more and a saturation concentration or less.

4. The biomolecule analysis method according to claim 1, wherein
the ammonium sulfate solution has an ammonium sulfate concentration of 0.01 M or more and 1 M or less.

5. The biomolecule analysis method according to claim 1 wherein
the ammonium sulfate solution has an ammonium sulfate concentration of 0.01 M or more and 0.2 M or less.

6. The biomolecule analysis method according to claim 1, wherein
the nanopore forming solution contains ammonium sulfate and other salt as salts, and
a ratio of a concentration of the ammonium sulfate to the total concentration of the salts is 5% or more and less than 100%.

7. The biomolecule analysis method according to claim 1, wherein the nanopore forming solution contains ammonium sulfate and another salt as salts, and a ratio of a concentration of the ammonium sulfate to the total concentration of the salts is 25% or more and less than 100%.

8. The biomolecule analysis method according to claim 1, wherein the nanopore forming solution contains ammonium sulfate and another salt as salts, and a ratio of a concentration of the ammonium sulfate to the total concentration of the salts is 50% or more and less than 100%.

9. The biomolecule analysis method according to claim 1, wherein the thin film contains at least one of SIN, SiO, and Si.

10. A biomolecule analysis method comprising:

preparing a biomolecule analysis device including a thin film having a nanopore, a first liquid tank and a second liquid tank separated by the thin film, a first electrode disposed in the first liquid tank, and a second electrode disposed in the second liquid tank; and measuring a current flowing between the first electrode and the second electrode by applying a voltage between the first electrode and the second electrode in a state where a measurement solution is enclosed in the first liquid tank and the second liquid tank, wherein the measurement solution contains ammonium ions and sulfate ions, wherein the measurement solution is an ammonium sulfate solution, and wherein the ammonium sulfate solution has an ammonium sulfate concentration of 0.01 M or more to suppress a noise in a baseline current.

11. The biomolecule analysis method according to claim 10, wherein the measurement solution further contains deoxynucleoside triphosphates (dNTP).

12. The biomolecule analysis method according to claim 11, wherein the deoxynucleoside triphosphates (dNTP) has a concentration of 100 μM or more.

13. The biomolecule analysis method according to claim 10, further comprising:

introducing a biomolecule into the measurement solution when measuring the current; and analyzing the biomolecule based on a measurement result of the current.

14. The biomolecule analysis method according to claim 13, wherein the biomolecule is a nucleic acid, a protein, or a nucleic acid in which a protein is modified.

15. A biomolecule analyzing reagent used for at least one of an application for forming a nanopore in a thin film by dielectric breakdown and an application for analyzing a biomolecule by passing the biomolecule through the nanopore, the biomolecule analyzing reagent comprising ammonium ions and sulfate ions, wherein the biomolecule analyzing reagent is an ammonium sulfate solution, and wherein the ammonium sulfate solution has an ammonium sulfate concentration of 0.01 M or more to suppress a noise in a baseline current.

16. The biomolecule analyzing reagent according to claim 15, wherein an ammonium sulfate concentration of the ammonium sulfate solution is 0.01 M or more and a saturation concentration or less.

17. The biomolecule analyzing reagent according to claim 16, wherein an ammonium sulfate concentration of the ammonium sulfate solution is 0.01 M or more and 1 M or less.

18. The biomolecule analyzing reagent according to claim 17, wherein an ammonium sulfate concentration of the ammonium sulfate solution is 0.01 M or more and 0.2 M or less.

19. The biomolecule analyzing reagent according to claim 15, wherein the biomolecule analyzing reagent contains ammonium sulfate and other salt as salts, and a ratio of a concentration of the ammonium sulfate to the total concentration of the salts is 5% or more and less than 100%.

20. The biomolecule analyzing reagent according to claim 19, wherein the ratio of the concentration of the ammonium sulfate to the total concentration of the salts is 25% or more and less than 100%.

21. The biomolecule analyzing reagent according to claim 20, wherein the ratio of the concentration of the ammonium sulfate to the total concentration of the salts is 50% or more and less than 100%.

22. The biomolecule analyzing reagent according to claim 15, further comprising deoxynucleoside triphosphates (dNTP).

23. The biomolecule analyzing reagent according to claim 22, wherein a concentration of the deoxynucleoside triphosphates (dNTP) is 100 μM or more.

24. A biomolecule analysis device comprising:

a thin film;

a first liquid tank and a second liquid tank separated by the thin film and each containing an electrolyte solution;

a first electrode disposed in the first liquid tank; and a second electrode disposed in the second liquid tank, wherein the electrolyte solution contains ammonium ions and sulfate ions, wherein the electrolyte solution is an ammonium sulfate solution, and wherein the ammonium sulfate solution has an ammonium sulfate concentration of 0.01 M or more to suppress a noise in a baseline current.

* * * * *